United States Patent
Dieye et al.

(10) Patent No.: US 10,039,708 B2
(45) Date of Patent: Aug. 7, 2018

(54) ORAL CARE COMPOSITION COMPRISING CUTTLEFISH BONE POWDER AND USES THEREOF

(71) Applicant: VISIONATUROLAB INC., Blainville, Quebec (CA)

(72) Inventors: Ousseynou Dieye, Laval (CA); Cheikh Ndiaye Ndime, Dakar (SN)

(73) Assignee: VISIONATUROLAB INC., Blainville QC (CA)

( * ) Notice: Subject to any disclaimer, the term of this patent is extended or adjusted under 35 U.S.C. 154(b) by 0 days.

(21) Appl. No.: 15/307,136

(22) PCT Filed: Apr. 28, 2015

(86) PCT No.: PCT/CA2015/000280
§ 371 (c)(1),
(2) Date: Oct. 27, 2016

(87) PCT Pub. No.: WO2015/164949
PCT Pub. Date: Nov. 5, 2015

(65) Prior Publication Data
US 2017/0056318 A1    Mar. 2, 2017

Related U.S. Application Data

(60) Provisional application No. 61/985,041, filed on Apr. 28, 2014.

(51) Int. Cl.
| | |
|---|---|
| *A61Q 11/00* | (2006.01) |
| *A61K 8/98* | (2006.01) |
| *A61K 8/19* | (2006.01) |
| *A61K 8/02* | (2006.01) |
| *A61K 8/24* | (2006.01) |
| *A61K 8/25* | (2006.01) |
| *A61K 8/26* | (2006.01) |

(52) U.S. Cl.
CPC ............ *A61K 8/987* (2013.01); *A61K 8/0241* (2013.01); *A61K 8/0279* (2013.01); *A61K 8/19* (2013.01); *A61K 8/24* (2013.01); *A61K 8/25* (2013.01); *A61K 8/26* (2013.01); *A61Q 11/00* (2013.01); *A61K 2800/28* (2013.01); *A61K 2800/412* (2013.01); *A61K 2800/48* (2013.01)

(58) Field of Classification Search
CPC ...... A61Q 11/00; A61K 28/00; A61K 28/412; A61K 8/0241
See application file for complete search history.

(56) References Cited

U.S. PATENT DOCUMENTS

| 451,371 | A | | 4/1891 | Ennes | |
|---|---|---|---|---|---|
| 2,059,396 | A | | 11/1936 | Ripert | |
| 5,424,060 | A | * | 6/1995 | Hauschild | A61K 8/22 424/52 |
| 2003/0180229 | A1 | * | 9/2003 | Kosti | A61K 8/22 424/53 |
| 2004/0018155 | A1 | * | 1/2004 | Hoagland | A61K 8/19 424/49 |
| 2007/0025929 | A1 | * | 2/2007 | Mohanty | A61K 8/02 424/52 |
| 2009/0186090 | A1 | * | 7/2009 | Zaidel | A61K 8/25 424/489 |
| 2009/0214451 | A1 | * | 8/2009 | Canham | A61K 8/02 424/57 |

FOREIGN PATENT DOCUMENTS

| CA | 2631472 | | 7/2007 | |
|---|---|---|---|---|
| CN | 1058903 | A * | 2/1992 | |
| CN | 1679493 | | 10/2005 | |
| CN | 101591593 | B * | 4/2012 | |
| CN | 104546623 | A * | 4/2015 | |
| FR | 579410 | | 10/1924 | |
| FR | 2788978 | | 8/2000 | |
| WO | WO 0216526 | A1 * | 2/2002 | ............... A61K 8/24 |
| WO | 2008001165 | | 1/2008 | |

OTHER PUBLICATIONS

International Preliminary Report on Patentability dated Aug. 31, 2016 for International Patent Application No. PCT/CA2015/000280.

European Search Report for Application No. EP 15786155.0 dated Sep. 25, 2017.

* cited by examiner

*Primary Examiner* — Tracy Liu

(74) *Attorney, Agent, or Firm* — McDonnell Boehnen Hulbert & Berghoff LLP

(57) ABSTRACT

The present document describes an oral care composition comprising a cuttlefish bone powder, comprising particles having more than 95% (w/w) calcium carbonate content, and a particle size of from about 60 microns to about 75 microns, and a suitable carrier, and uses of said composition for oral hygiene.

21 Claims, 3 Drawing Sheets
(1 of 3 Drawing Sheet(s) Filed in Color)

ORAL CARE COMPOSITION COMPRISING CUTTLEFISH BONE POWDER AND USES THEREOF

CROSS-REFERENCE TO RELATED APPLICATIONS

This application is a US National Phase application under 35 USC § 371 of PCT/CA2015/000280, filed Apr. 28, 2015, which claims priority from and the benefit of U.S. Provisional Application No. 61/985,041, filed on Apr. 28, 2015, the specifications of which are hereby incorporated by reference in their entireties.

BACKGROUND OF THE INVENTION

Field of the Invention

The subject matter disclosed generally relates to oral care compositions and uses thereof, and more specifically, the subject matter disclosed relates to oral care compositions comprising cuttlefish bone powder and uses thereof.

Description of Related Art

Synthetic as well as natural agents have been used for cleansing purposes. Soaps, surfactants and synthetic detergents have been used for decades for mouth cleansing. The objective of cleansing is to remove tartar, food particles, and potentially harmful microorganisms from the oral cavity.

Most of the currently available oral care compositions that are helpful of tartar contain small quantities of chemicals which are considered dangerous for the health of the user, such as compounds containing fluoride ions (e.g. sodium fluoride, sodium monofluorophosphate, tin fluoride, hydrofluoride nicomethanol, amine fluoride, and other derivatives of fluoride), zinc ions, peroxigen compounds (e.g., hydrogen peroxide), enzymes, nitrates, borate derivatives, preservative agents, antibacterials and antifungals, such as trichiosan. These ingredients, although present in small amounts that have no immediate harmful effects, are a growing health concerns for the users of these products, which would prefer products that do not contain them.

Thus, there is a need for oral care formulations containing no harmful chemicals, providing efficient oral cleansing.

SUMMARY OF THE INVENTION

It is against the above background that the present invention provides certain advantages and advancements over the prior art.

According to an embodiment, there is provided an oral care composition comprising:
  a cuttlefish bone powder, comprising particles having more than 95% (w/w) calcium carbonate content, and a particle size of from about 60 microns to about 75 microns, and
  a suitable carrier.

The calcium carbonate content may be from about 95% to about 99.9%.

The particle size may be about 72 microns.

The cuttlefish bone powder may have a relative density of about 0.15 to about 1.30 g/L.

The cuttlefish bone powder may have a relative density of about 1.22 g/L.

The cuttlefish bone powder may have a porosity of about 0.25 to about 0.45.

The cuttlefish bone powder may have a porosity of about 0.39.

The cuttlefish bone powder may have a suspension time of about 5 h to about 8 h.

The cuttlefish bone powder may have a suspension time of about 6.5 h.

The cuttlefish bone powder may be from about 0.100% to about 20% (w/w) of the composition.

The oral care composition may be further comprising an abrasive.

The abrasive may be a colloidal calcium, a colloidal silica, a hydrated silica, a sodium bicarbonate ($NaHCO_3$), aluminum hydroxide ($Al(OH)_3$), calcium carbonate ($CaCO_3$), a calcium hydrogen phosphate ($CaHPO_4.2H_2O$), an anhydrous calcium hydrogen phosphate, a silica, a zeolites, and hydroxyapatite ($Ca_5(PO_4)_3OH$), or a combination thereof.

The abrasive may be from about 0.100% to about 0.325% (w/w) of the composition.

The colloidal silica may be from about 0.100% to about 0.275% (w/w).

The colloidal silica may be from about 0.02% to about 0.08% (w/w) of the composition.

The oral care composition may be further comprising a thickening agent.

The thickening agent may be a natural gum obtained from seaweeds; a natural gum obtained from non-marine botanical resource, a natural gum produced by bacterial fermentation, a starch, a pectin, a carboxymethyl cellulose, a hydroxypropyl cellulose, a methyl cellulose, a gelatin or a combination thereof.

The natural gums obtained from seaweeds may be chosen from agar (E406), alginic acid (E400), Sodium alginate (E401), potassium alginate, ammonium alginate, calcium alginate, carrageenan (E407), or a combination thereof.

The natural gum obtained from non-marine botanical resource may be chosen from acacia gum, gum arabic (E414), gum ghatti, gum tragacanth (E413), karaya gum (E416), guar gum (E412), locust bean gum (E410), beta-glucan, chicle gum, dammar gum, Glucomannan (E425), mastic gum, *psyllium* seed husks, spruce gum, tara gum (E417), or a combination thereof.

The natural gum produced by bacterial fermentation may be chosen from gellan gum (E418), Xanthan gum (E415), or a combination thereof.

The thickening agent may be from about 2% to about 66% (w/w) of the composition.

The thickening agent may be about 2.2% (w/w) of the composition.

The oral care composition may be further comprising a humectant.

The humectant may be propylene glycol, hexylene glycol, butylene glycol, glyceryl triacetate, neoagarobiose, a sugar polyol, a polymeric polyol, *quillaia*, lactic acid, urea, glycerin, aloe vera gel, MP Diol, an alpha hydroxy acid, and honey.

The sugar polyols may be chosen from glycerol, sorbitol, xylitol, maltitol, and a combination thereof.

The polymeric polyol may be polydextrose, polyethylene glycol, polypropylene glycol, poly(tetramethylene ether) glycol, and a combination thereof.

The alpha hydroxy acid may be lactic acid.

The humectant may be glycerin.

The humectant may be from about 2% to about 5% (w/w) of the composition.

The oral care composition may be further comprising an emulsifier.

The emulsifier may be lecithin, a vegetal pulp powder, a sodium citrate and citric acid, or a combination thereof.

The vegetal pulp powder may be chosen from citrus pulp powder, baobab pulp powder, mango pulp powder, tomato pulp powder, pumpkin pulp powder, guava pulp powder, papaya pulp powder and beet pulp powder, or a combination thereof.

The sodium citrate may be trisodium citrate.

The emulsifier may be from about 4% to about 10% (w/w) of the composition.

The oral composition may be further comprising a surfactant.

The surfactant may be chosen from sodium lauryl sulfate, ammonium lauryl sulfate, sodium N-lauryl sarcosinate, sodium lauryl sulfoacetate, or a combination thereof.

The surfactant may be from about 1% to about 3% (w/w) of the composition.

The oral composition may be further comprising a pH regulator.

The pH regulator may be chosen from citric acid and its derivatives, phosphoric acid and its derivatives, trisodium phosphate, sodium citrate, lactic acid, bicarbonic acid, or a combination thereof.

The pH regulator may be from about 0.1% to about 0.25% (w/w) of the composition.

The oral composition may be further comprising a preservative.

The preservative may be chosen from a sorbitan sesquioleate derivative, sodium benzoate, benzoic acid, a eucalyptus extract, or a combination thereof.

The preservative may be from about 0.2% to about 2% (w/w) of the composition.

The oral composition may be further comprising a solvent.

The solvent may be chosen from water, ethanol, isopropanol, sorbitol and glycerin.

The solvent may be from about 60% to about 99% (w/w) of the composition.

The oral composition may be further comprising an antimicrobial agent.

The antimicrobial agent may be chosen from a natural essential oil, an antimicrobial phenolic compound, or a combination thereof.

The natural essential oil may be chosen from oils of anise, lemon oil, orange oil, oregano, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea origanum oil, Hydastis carradensis oil, Berberidaceae daceae oil, Ratanhiae and Curcuma longa oil, sesame oil, macadamia nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang.

The antimicrobial phenolic compound may be chosen from carvacrol, thymol, eugenol, eucalyptol, menthol, or a combination thereof.

The antimicrobial agent may be from about 0.01% to about 10% (w/w) of the composition.

According to another embodiment, there is provided a use of an oral composition of the present invention may be for oral hygiene.

According to another embodiment, there is provided a method of cleaning an oral cavity comprising applying the oral composition of the present invention to an oral cavity.

The cleaning of an oral cavity may be for teeth cleansing, teeth whitening, and removal of dental tartar, or a combination thereof.

According to another embodiment, there is provided a method for preparing a cuttlefish bone powder comprising the steps of:
  a) grinding a cuttlefish bone to obtain a coarse cuttlefish bone powder;
  b) sieving the coarse bone powder to obtain a first cuttlefish bone powder having particle size from about 60 microns to about 75 microns;
  c) mild demineralization of the first cuttlefish bone powder having particle size from about 60 microns to about 75 microns at a pH of about 4.5 to about 5.5, at a temperature sufficient and for a time sufficient to obtain a demineralized cuttlefish bone powder;
  d) washing the demineralized cuttlefish bone powder until a neutral pH may be reached, and
  e) drying the demineralized cuttlefish bone powder.

According to another embodiment, there is provided a method for preparing a cuttlefish bone powder comprising the steps of:
  a) mild demineralization of a cuttlefish bone powder having particle size from about 60 microns to about 75 microns at a pH of about 4.5 to about 5.5, at a temperature sufficient and for a time sufficient to obtain a demineralized cuttlefish bone powder.

The method may be further comprising step b) washing the demineralized cuttlefish bone powder until a neutral pH may be reached.

The method may be further comprising step c) drying the demineralized cuttlefish bone powder.

The mild demineralization may be in ammonium chloride.

The concentration of ammonium chloride may be from about 0.1 M to about 1 M.

The mild demineralization may be at a pH of about 4.5.

The mild demineralization may be at a pH of about 4.9.

The mild demineralization may be at a pH of about 4.86.

The mild demineralization may be at a temperature from about 65° C. to about 75° C.

The washing the demineralized cuttlefish bone powder may be in distilled water.

The drying the demineralized cuttlefish bone powder may be at about 200° C. to about 220° C.

The drying the demineralized cuttlefish bone powder may be at about 200° C.

The drying the demineralized cuttlefish bone powder may be for about 30 min to about 60 min.

The drying the demineralized cuttlefish bone powder may be for about 55 min.

According to another embodiment, there is provided a cuttlefish bone powder obtained by the method of the present invention.

According to another embodiment, there is provided a cuttlefish bone powder, comprising particles having more than 95% (w/w) calcium carbonate content, and a particle size of from about 60 microns to about 75 microns, a relative density of about 0.15 to about 1.30 g/L, and a porosity of about 0.25 to about 0.45.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further features and advantages of the present disclosure will become apparent from the following detailed description, taken in combination with the appended drawing, in which.

Figure 1:
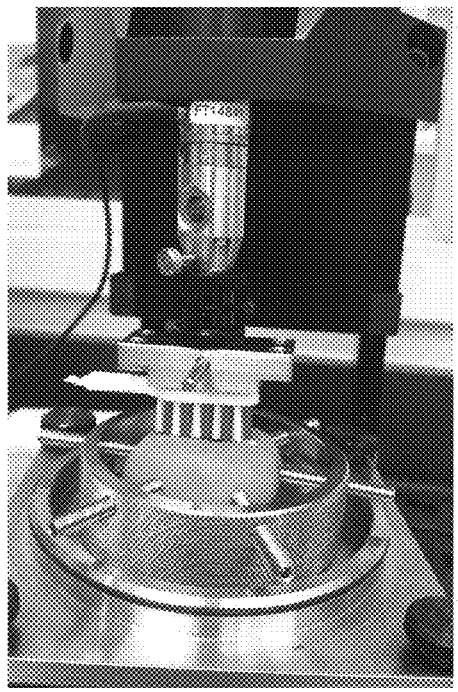
FIGS. 1A-D illustrate a tooth brushing machine having a tooth mounted thereon.
Figure 1:
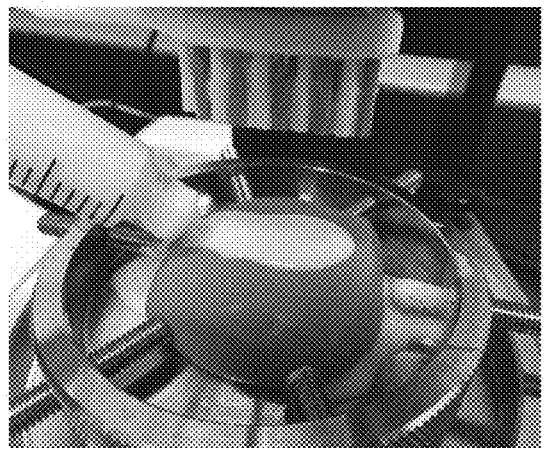
Figure 1:
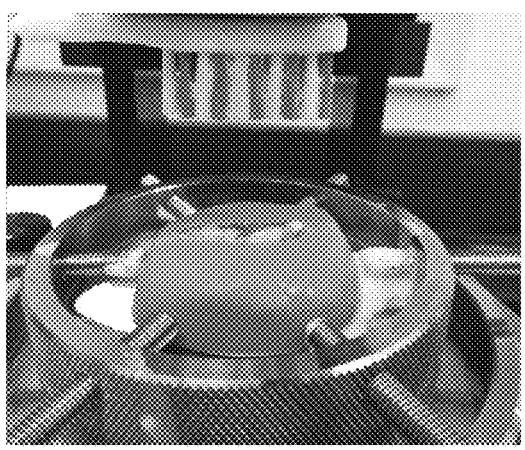
Figure 1:
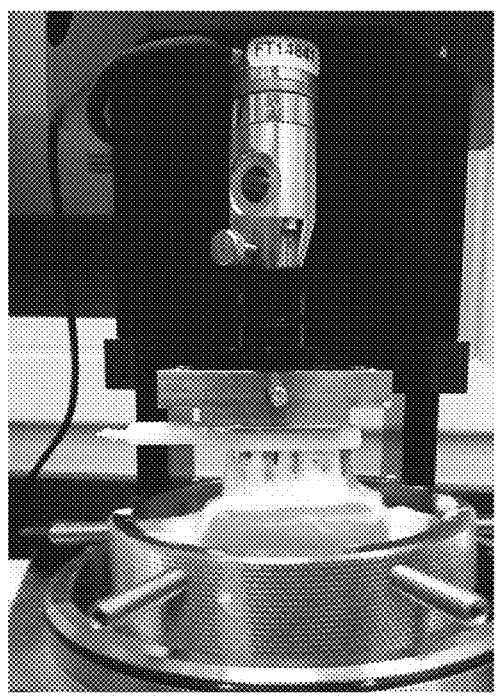

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature and not as restrictive and the full scope of the subject matter is set forth in the claims.

DETAILED DESCRIPTION OF THE INVENTION

All publications, patents and patent applications cited herein are hereby expressly incorporated by reference for all purposes.

Before describing the present invention in detail, a number of terms will be defined. As used herein, the singular forms "a", "an", and "the" include plural referents unless the context clearly dictates otherwise.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

In embodiments there are disclosed an oral care compositions. The compositions of the present invention are oral care compositions containing as an ingredient cuttlefish bone powder obtained from ground bones. Cuttlefish are marine animals of the order Sepiida. They belong to the class Cephalopoda, which also includes squid, octopuses, and nautiluses. "Cuttle" is a reference to their unique internal shell, the cuttlebone. Despite their name, cuttlefish are not fish but mollusks.

A cuttlefish possesses an internal structure called the cuttlebone, which is porous and is made of aragonite. Aragonite is a carbonate mineral, one of the two common, naturally occurring, crystal forms of calcium carbonate, $CaCO_3$ (the other form being the mineral calcite). It is formed by biological and physical processes, including precipitation from marine and freshwater environments.

Aragonite's crystal lattice differs from that of calcite, resulting in a different crystal shape, an orthorhombic system with acicular crystals. Repeated twinning results in pseudo-hexagonal forms. Aragonite may be columnar or fibrous, occasionally in branching stalactitic forms called flos-ferri ("flowers of iron") from their association with the ores at the Carinthian iron mines.

Aragonite forms naturally in almost all mollusk shells, and as the calcareous endoskeleton of warm- and cold-water corals (Scleractinia). Several serpulids have aragonitic tubes. Because the mineral deposition in mollusk shells is strongly biologically controlled, some crystal forms are distinctively different from those of inorganic aragonite. In some mollusks, the entire shell is aragonite; in others, aragonite forms only discrete parts of a bimineralic shell (aragonite plus calcite). Aragonite also forms in the ocean and in caves as inorganic precipitates called marine cements and speleothems, respectively. The nacreous layer of the aragonite fossil shells of some extinct ammonites forms an iridescent material called ammolite. Ammolite is primarily aragonite with impurities that make it iridescent and valuable as a gemstone.

The particles of the cuttlefish bone powder used in the present invention may be from about 60 microns to about 75 microns, or from about 60 microns to about 74 microns, or from about 60 microns to about 73 microns, or from about 60 microns to about 72 microns, or from about 60 microns to about 71 microns, or from about 60 microns to about 70 microns, or from about 60 microns to about 69 microns, or from about 60 microns to about 68 microns, or from about 60 microns to about 67 microns, or from about 60 microns to about 66 microns, or from about 60 microns to about 65 microns, or from about 60 microns to about 64 microns, or from about 60 microns to about 63 microns, or from about 60 microns to about 62 microns, or from about 60 microns to about 61 microns. Preferably, the particle size is 72 microns. The favored abrasion ration value is between 0 and 88 in accordance to the DESAUTELS and LABRECHE 1999 scale. The abrasiveness scale of DESAUTELS and LABRECHE varies as follows for toothpaste: 1) bit abrasive: 0% to 88%; 2) abrasive to medium abrasive: 88% to 100% and 3) very abrasive: >100%.

The particles have been treated with a mild demineralization treatment, for example in ammonium chloride or ammonium acetate, at pH from about 4.5 to about 5.5, or from about 4.5 to about 5.4, or from about 4.5 to about 5.3, or from about 4.5 to about 5.2, or from about 4.5 to about 5.1, or from about 4.5 to about 5.0, or from about 4.5 to about 4.9, or from about 4.5 to about 4.8, or from about 4.5 to about 4.7, or from about 4.5 to about 4.6, or from about 4.6 to about 5.5, or from about 4.6 to about 5.4, or from about 4.6 to about 5.3, or from about 4.6 to about 5.2, or from about 4.6 to about 5.1, or from about 4.6 to about 5.0, or from about 4.6 to about 4.9, or from about 4.6 to about 4.8, or from about 4.6 to about 4.7, or from about 4.7 to about 5.5, or from about 4.7 to about 5.4, or from about 4.7 to about 5.3, or from about 4.7 to about 5.2, or from about 4.7 to about 5.1, or from about 4.7 to about 5.0, or from about 4.7 to about 4.9, or from about 4.7 to about 4.8, or from about 4.8 to about 5.5, or from about 4.8 to about 5.4, or from about 4.8 to about 5.3, or from about 4.8 to about 5.2, or from about 4.8 to about 5.1, or from about 4.8 to about 5.0, or from about 4.8 to about 4.9, or from about 4.9 to about 5.5, or from about 4.9 to about 5.4, or from about 4.9 to about 5.3, or from about 4.9 to about 5.2, or from about 4.9 to about 5.1, or from about 4.9 to about 5.0, or from about 5.0 to about 5.5, or from about 5.0 to about 5.4, or from about 5.0 to about 5.3, or from about 5.0 to about 5.2, or from about 5.0 to about 5.1, or from about 5.1 to about 5.5, or from about 5.1 to about 5.4, or from about 5.1 to about 5.3, or from about 5.1 to about 5.2, or from about 5.2 to about 5.5, or from about 5.2 to about 5.4, or from about 5.2 to about 5.3, or from about 5.3 to about 5.5, or from about 5.3 to about 5.4, or from about 5.4 to about 5.5, and preferably pH about 4.75, 4.76, 4.77, 4.78, 4.79, 4.80, 4.81, 4.82, 4.83, 4.84, 4.85, 4.86, 4.87, 4.88, 4.89, 4.90, and most preferably 4.86 in order to solubilize unwanted magnesium, ammonia, iron and zinc compounds present in the bone material, and increase the calcium carbonate content of the powder of the present invention. Indeed, the bone powder used in the present invention comprises a high content in calcium; containing at least 95% calcium carbonate, with reduced amounts of magnesium, zinc, iron and ammonia containing derivatives. According to embodiments, the calcium carbonate of the cuttlefish bone powder particles may be at least 95%, at least 95.5%, at least 96%, at least 96.5%, at least 97%, at least 97.5%, at least 98%, at least 98.5%, at least 99%, or from about 95% to 99% (w/w), or from about 95% to 98.5% (w/w), or from about 95% to about 98%, or from about 95% to 97.5% (w/w), or from about 95% to about 97%, or from about 95% to 96.5% (w/w), or from about 95% to about 96%, or from about 95% to 95.5% (w/w), or from about 95.5% to 99% (w/w), or from about 95.5% to 98.5% (w/w), or from about 95.5% to about 98%, or from about 95.5% to 97.5% (w/w), or from about 95.5% to about 97%, or from about 95.5% to 96.5% (w/w), or from about 95.5% to about 96%, or from about 96% to 99% (w/w), or from about 96% to 98.5% (w/w), or from about 96% to about 98%, or from about 96% to 97.5% (w/w), or from about 96% to about 97%, or from about 96% to 96.5% (w/w), or from about 96.5% to 99% (w/w), or from about 96.5% to 98.5% (w/w), or from about 96.5% to about 98%, or from about 96.5% to 97.5% (w/w), or from about 96.5% to about 97%, or from about 97% to 99% (w/w), or from about 97% to 98.5% (w/w), or from about 97% to about 98%, or from about 97% to 97.5% (w/w), or from about 97.5% to 99% (w/w), or from about 97.5% to 98.5% (w/w), or from about 97.5% to about 98%, or from about 98% to 99% (w/w), or from about 98% to 98.5% (w/w), or from about 98.5% to 99% (w/w).

According to another embodiment, the relative density of the cuttlefish bone powder is from about 0.15 to about 1.30, or from about 0.20 to about 1.30, or from about 0.25 to about 1.30, or from about 0.30 to about 1.30, or from about 0.35 to about 1.30, or from about 0.40 to about 1.30, or from about 0.45 to about 1.30, or from about 0.50 to about 1.30, or from about 0.55 to about 1.30, or from about 0.60 to about 1.30, or from about 0.65 to about 1.30, or from about 0.70 to about 1.30, or from about 0.75 to about 1.30, or from about 0.80 to about 1.30, or from about 0.85 to about 1.30, or from about 0.90 to about 1.30, or from about 0.95 to about 1.30, or from about 1.00 to about 1.30, or from about 1.00 to about 1.30, or from about 1.10 to about 1.30, or from about 1.15 to about 1.30, or from about 1.20 to about 1.30, or from about 1.25 to about 1.30, or from about 0.15 to about 1.25, or from about 0.20 to about 1.25, or from about 0.25 to about 1.25, or from about 0.30 to about 1.25, or from about 0.35 to about 1.25, or from about 0.40 to about 1.25, or from about 0.45 to about 1.25, or from about 0.50 to about 1.25, or from about 0.55 to about 1.25 or from about 0.60 to about 1.25, or from about 0.65 to about 1.25, or from about 0.70 to about 1.25, or from about 0.75 to about 1.25, or from about 0.80 to about 1.25, or from about 0.85 to about 1.25, or from about 0.90 to about 1.25, or from about 0.95 to about 1.25, or from about 1.00 to about 1.25, or from about 1.05 to about 1.25, or from about 1.10 to about 1.25, or from about 1.15 to about 1.25, or from about 1.20 to about 1.25, or from about 0.15 to about 1.20, or from about 0.20 to about 1.20, or from about 0.25 to about 1.20, or from about 0.30 to about 1.20, or from about 0.35 to about 1.20, or from about 0.40 to about 1.20, or from about 0.45 to about 1.20, or from about 0.50 to about 1.20, or from about 0.55 to about 1.20, or from about 0.60 to about 1.20, or from about 0.65 to about 1.20, or from about 0.70 to about 1.20, or from about 0.75 to about 1.20, or from about 0.80 to about 1.20, or from about 0.85 to about 1.20, or from about 0.90 to about 1.20, or from about 0.95 to about 1.20, or from about 1.00 to about 1.20, or from about 1.05 to about 1.20, or from about 1.10 to about 1.20, or from about 1.15 to about 1.20, or from about 0.15 to about 1.15, or from about 0.20 to about 1.15, or from about 0.25 to about 1.15, or from about 0.30 to about 1.15, or from about 0.35 to about 1.15, or from about 0.40 to about 1.15, or from about 0.45 to about 1.15, or from about 0.50 to about 1.15, or from about 0.55 to about 1.15, or from about 0.60 to about 1.15, or from about 0.65 to about 1.15, or from about 0.70 to about 1.15, or from about 0.75 to about 1.15, or from about 0.80 to about 1.15, or from about 0.85 to about 1.15, or from about 0.90 to about 1.15, or from about 0.95 to about 1.15, or from about 1.00 to about 1.15, or from about 1.05 to about 1.15, or from about 1.10 to about 1.15, or from about 0.15 to about 1.10, or from about 0.20 to about 1.10, or from about 0.25 to about 1.10, or from about 0.30 to about 1.10, or from about 0.35 to about 1.10, or from about 0.40 to about 1.10, or from about 0.45 to about 1.10, or from about 0.50 to about 1.10, or from about 0.55 to about 1.10, or from about 0.60 to about 1.10, or from about 0.65 to about 1.10, or from about 0.70 to about 1.10, or from about 0.75 to about 1.10, or from about 0.80 to about 1.10, or from about 0.85 to about 1.10, or from about 0.90 to about 1.10, or from about 0.95 to about 1.10, or from about 1.00 to about 1.10, or from about 1.05 to about 1.10, or from about 0.15 to about 1.05, or from about 0.20 to about 1.05, or from about 0.25 to about 1.05, or from about 0.30 to about 1.05, or from about 0.35 to about 1.05, or from about 0.40 to about 1.05, or from about 0.45 to about 1.05, or from about 0.50 to about 1.05, or from about 0.55 to about 1.05, or from about 0.60 to about 1.05, or from about 0.65 to about 1.05, or from about 0.70 to about 1.05, or from about 0.75 to about 1.05, or from about 0.80 to about 1.05, or from about 0.85 to about 1.05, or from about 0.90 to about 1.05, or from about 0.95 to about 1.05, or from about 1.00 to about 1.05, or from about 0.15 to about 1.00, or from about 0.20 to about 1.00, or from about 0.25 to about 1.00, or from about 0.30 to about 1.00, or from about 0.35 to about 1.00, or from about 0.40 to about 1.00, or from about 0.45 to about 1.00, or from about 0.50 to about 1.00, or from about 0.55 to about 1.00, or from about 0.60 to about 1.00, or from about 0.65 to about 1.00, or from about 0.70 to about 1.00, or from about 0.75 to about 1.00, or from about 0.80 to about 1.00, or from about 0.85 to about 1.00, or from about 0.90 to about 1.00, or from about 0.95 to about 1.00, or from about 0.15 to about 0.95, or from about 0.20 to about 0.95, or from about 0.25 to about 0.95, or from about 0.30 to about 0.95, or from about 0.35 to about 0.95, or from about 0.40 to about 0.95, or from about 0.45 to about 0.95, or from about 0.50 to about 0.95, or from about 0.55 to about 0.95, or from about 0.60 to about 0.95, or from about 0.65 to about 0.95, or from about 0.70 to about 0.95, or from about 0.75 to about 0.95, or from about 0.80 to about 0.95, or from about 0.85 to about 0.95, or from about 0.90 to about 0.95, or from about 0.15 to about 0.90, or from about 0.20 to about 0.90, or from about 0.25 to about 0.90, or from about 0.30 to about 0.90, or from about 0.35 to about 0.90, or from about 0.40 to about 0.90, or from about 0.45 to about 0.90, or from about 0.50 to about 0.90, or from about 0.55 to about 0.90, or from about 0.60 to about 0.90, or from about 0.65 to about 0.90, or from about 0.70 to about 0.90, or from about 0.75 to about 0.90, or from about 0.80 to about 0.90, or from about 0.85 to about 0.90, or from about 0.15 to about 0.85, or from about 0.20 to about 0.85, or from about 0.25 to about 0.85, or from about 0.30 to about 0.85, or from about 0.35 to about 0.85, or from about 0.40 to about 0.85, or from about 0.45 to about 0.85, or from about 0.50 to about 0.85, or from about 0.55 to about 0.85, or from about 0.60 to about 0.85, or from about 0.65 to about 0.85, or from about 0.70 to about 0.85, or from about 0.75 to about 0.85, or from about 0.80 to about 0.85, or from about 0.15 to about 0.80, or from about 0.20 to about 0.80, or from about 0.25 to about 0.80, or from about 0.30 to about 0.80, or from about 0.35 to about 0.80, or from about 0.40 to about 0.80, or from about 0.45 to about 0.80, or from about 0.50 to about 0.80, or from about 0.55 to about 0.80, or from about 0.60 to about 0.80, or from about 0.65 to about 0.80, or from about 0.70 to about 0.80, or from about 0.75 to about 0.80, or from about 0.15 to about 0.75, or from about 0.20 to about 0.75, or from about 0.25 to about 0.75, or from about 0.30 to about 0.75, or from about 0.35 to about 0.75, or from about 0.40 to about 0.75, or from about 0.45 to about 0.75, or from about 0.50 to about 0.75, or from about 0.55 to about 0.75, or from about 0.60 to about 0.75, or from about 0.65 to about 0.75, or from about 0.70 to about 0.75, or from about 0.75 to about 0.80, or from about 0.15 to about 0.70, or from about 0.20 to about 0.70, or from about 0.25 to about 0.70, or from about 0.30 to about 0.70, or from about 0.35 to about 0.70, or from about 0.40 to about 0.70, or from about 0.45 to about 0.70, or from about 0.50 to about 0.70, or from about 0.55 to about 0.70, or from about 0.60 to about 0.70, or from about 0.65 to about 0.70, or from about 0.15 to about 0.65, or from about 0.20 to about 0.65, or from about 0.25 to about 0.65, or from about 0.30 to about 0.65, or from about 0.35 to about 0.65, or from about 0.40 to about 0.65, or from about 0.45 to about 0.65, or from about 0.50 to about 0.65, or from about 0.55 to about 0.65, or from about 0.60 to about 0.65, or from about 0.15 to about 0.60, or from about 0.20 to about 0.60, or from about 0.25 to about 0.60, or from about 0.30 to about 0.60, or from about 0.35 to about 0.60, or from about 0.40 to about 0.60, or from about 0.45 to about 0.60, or from about 0.50 to about 0.60, or from about 0.55 to about 0.60, or from about 0.15 to about 0.55, or from about 0.20 to about 0.55, or from about 0.25 to about 0.55, or from about 0.30 to about 0.55, or from about 0.35 to about 0.55, or from about 0.40 to about 0.55, or from about 0.45 to about 0.55, or from about 0.50 to about 0.55, or from about 0.15 to about 0.50, or from about 0.20 to about 0.50, or from about 0.25 to about 0.50, or from about 0.30 to about 0.50, or from about 0.35 to about 0.50, or from about 0.40 to about 0.50, or from about 0.45 to about 0.50, or from about 0.50 to about 0.50, or from about 0.15 to about 0.45, or from about 0.20 to about 0.45, or from about 0.25 to about 0.45, or from about 0.30 to about 0.45, or from about 0.35 to about 0.45, or from about 0.40 to about 0.45, or from about 0.15 to about 0.40, or from about 0.20 to about 0.40, or from about 0.25 to about 0.40, or from about 0.30 to about 0.40, or from about 0.35 to about 0.40, or from about 0.40 to about 0.40, or from about 0.15 to about 0.35, or from about 0.20 to about 0.35, or from about 0.25 to about 0.35, or from about 0.30 to about 0.35, or from about 0.15 to about 0.30, or from about 0.20 to about 0.30, or from about 0.25 to about 0.30, or from about 0.15 to about 0.25, or from about 0.20 to about 0.25, or from about 0.15 to about 0.20, or from about 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30 g/L. Preferably the density of about 1.22 g/L. The density and powder flowability influences its dispersion in the formulation of the present invention, and the denser the cuttlefish bone powder, the more it tends to agglomerate to the bottom of the package over time.

According to another embodiment, the porosity of the cuttlefish bone powder is from about 0.25 to about 0.45, or from about 0.26 to about 0.45, or from about 0.27 to about 0.45, or from about 0.28 to about 0.45, or from about 0.29 to about 0.45, or from about 0.30 to about 0.45, or from about 0.31 to about 0.45, or from about 0.32 to about 0.45, or from about 0.33 to about 0.45, or from about 0.34 to about 0.45, or from about 0.35 to about 0.45, or from about 0.36 to about 0.45, or from about 0.37 to about 0.45, or from about 0.38 to about 0.45, or from about 0.39 to about 0.45, or from about 0.40 to about 0.45, or from about 0.41 to about 0.45, or from about 0.42 to about 0.45, or from about 0.43 to about 0.45, or from about 0.44 to about 0.45, is from about 0.25 to about 0.44, or from about 0.26 to about 0.44, or from about 0.27 to about 0.44, or from about 0.28 to about 0.44, or from about 0.29 to about 0.44, or from about 0.30 to about 0.44, or from about 0.31 to about 0.44, or from about 0.32 to about 0.44, or from about 0.33 to about 0.44, or from about 0.34 to about 0.44, or from about 0.35 to about 0.44, or from about 0.36 to about 0.44, or from about 0.37 to about 0.44, or from about 0.38 to about 0.44, or from about 0.39 to about 0.44, or from about 0.40 to about 0.44, or from about 0.41 to about 0.44, or from about 0.42 to about 0.44, or from about 0.43 to about 0.44, is from about 0.25 to about 0.43, or from about 0.26 to about 0.43, or from about 0.27 to about 0.43, or from about 0.28 to about 0.43, or from about 0.29 to about 0.43, or from about 0.30 to about 0.43, or from about 0.31 to about 0.43, or from about 0.32 to about 0.43, or from about 0.33 to about 0.43, or from about 0.34 to about 0.43, or from about 0.35 to about 0.43, or from about 0.36 to about 0.43, or from about 0.37 to about 0.43, or from about 0.38 to about 0.43, or from about 0.39 to about 0.43, or from about 0.40 to about 0.43, or from about 0.41 to about 0.43, or from about 0.42 to about 0.43, is from about 0.25 to about 0.42, or from about 0.26 to about 0.42, or from about 0.27 to about 0.42, or from about 0.28 to about 0.42, or from about 0.29 to about 0.42, or from about 0.30 to about 0.42, or from about 0.31 to about 0.42, or from about 0.32 to about 0.42, or from about 0.33 to about 0.42, or from about 0.34 to about 0.42, or from about 0.35 to about 0.42, or from about 0.36 to about 0.42, or from about 0.37 to about 0.42, or from about 0.38 to about 0.42, or from about 0.39 to about 0.42, or from about 0.40 to about 0.42, or from about 0.41 to about 0.42, is from about 0.25 to about 0.41, or from about 0.26 to about 0.41, or from about 0.27 to about 0.41, or from about 0.28 to about 0.41, or from about 0.29 to about 0.41, or from about 0.30 to about 0.41, or from about 0.31 to about 0.41, or from about 0.32 to about 0.41, or from about 0.33 to about 0.41, or from about 0.34 to about 0.41, or from about 0.35 to about 0.41, or from about 0.36 to about 0.41, or from about 0.37 to about 0.41, or from about 0.38 to about 0.41, or from about 0.39 to about 0.41, or from about 0.40 to about 0.41, is from about 0.25 to about 0.40, or from about 0.26 to about 0.40, or from about 0.27 to about 0.40, or from about 0.28 to about 0.40, or from about 0.29 to about 0.40, or from about 0.30 to about 0.40, or from about 0.31 to about 0.40, or from about 0.32 to about 0.40, or from about 0.33 to about 0.40, or from about 0.34 to about 0.40, or from about 0.35 to about 0.40, or from about 0.36 to about 0.40, or from about 0.37 to about 0.40, or from about 0.38 to about 0.40, or from about 0.39 to about 0.40, is from about 0.25 to about 0.39, or from about 0.26 to about 0.39, or from about 0.27 to about 0.39, or from about 0.28 to about 0.39, or from about 0.29 to about 0.39, or from about 0.30 to about 0.39, or from about 0.31 to about 0.39, or from about 0.32 to about 0.39, or from about 0.33 to about 0.39, or from about 0.34 to about 0.39, or from about 0.35 to about 0.39, or from about 0.36 to about 0.39, or from about 0.37 to about 0.39, or from about 0.38 to about 0.39, is from about 0.25 to about 0.38, or from about 0.26 to about 0.38, or from about 0.27 to about 0.38, or from about 0.28 to about 0.38, or from about 0.29 to about 0.38, or from about 0.30 to about 0.38, or from about 0.31 to about 0.38, or from about 0.32 to about 0.38, or from about 0.33 to about 0.38, or from about 0.34 to about 0.38, or from about 0.35 to about 0.38, or from about 0.36 to about 0.38, or from about 0.37 to about 0.38, is from about 0.25 to about 0.37, or from about 0.26 to about 0.37, or from about 0.27 to about 0.37, or from about 0.28 to about 0.37, or from about 0.29 to about 0.37, or from about 0.30 to about 0.37, or from about 0.31 to about 0.37, or from about 0.32 to about 0.37, or from about 0.33 to about 0.37, or from about 0.34 to about 0.37, or from about 0.35 to about 0.37, or from about 0.36 to about 0.37, is from about 0.25 to about 0.36, or from about 0.26 to about 0.36, or from about 0.27 to about 0.36, or from about 0.28 to about 0.36, or from about 0.29 to about 0.36, or from about 0.30 to about 0.36, or from about 0.31 to about 0.36, or from about 0.32 to about 0.36, or from about 0.33 to about 0.36, or from about 0.34 to about 0.36, or from about 0.35 to about 0.36, is from about 0.25 to about 0.35, or from about 0.26 to about 0.35, or from about 0.27 to about 0.35, or from about 0.28 to about 0.35, or from about 0.29 to about 0.35, or from about 0.30 to about 0.35, or from about 0.31 to about 0.35, or from about 0.32 to about 0.35, or from about 0.33 to about 0.35, or from about 0.34 to about 0.35, is from about 0.25 to about 0.34, or from about 0.26 to about 0.34, or from about 0.27 to about 0.34, or from about 0.28 to about 0.34, or from about 0.29 to about 0.34, or from about 0.30 to about 0.34, or from about 0.31 to about 0.34, or from about 0.32 to about 0.34, or from about 0.33 to about 0.34, is from about 0.25 to about 0.33, or from about 0.26 to about 0.33, or from about 0.27 to about 0.33, or from about 0.28 to about 0.33, or from about 0.29 to about 0.33, or from about 0.30 to about 0.33, or from about 0.31 to about 0.33, or from about 0.32 to about 0.33, is from about 0.25 to about 0.32, or from about 0.26 to about 0.32, or from about 0.27 to about 0.32, or from about 0.28 to about 0.32, or from about 0.29 to about 0.32, or from about 0.30 to about 0.32, or from about 0.31 to about 0.32, is from about 0.25 to about 0.31, or from about 0.26 to about 0.31, or from about 0.27 to about 0.31, or from about 0.28 to about 0.31, or from about 0.29 to about 0.31, or from about 0.30 to about 0.31, is from about 0.25 to about 0.30, or from about 0.26 to about 0.30, or from about 0.27 to about 0.30, or from about 0.28 to about 0.30, or from about 0.29 to about 0.30, is from about 0.25 to about 0.29, or from about 0.26 to about 0.29, or from about 0.27 to about 0.29, or from about 0.28 to about 0.29, is from about 0.25 to about 0.28, or from about 0.26 to about 0.28, or from about 0.27 to about 0.28, is from about 0.25 to about 0.27, or from about 0.26 to about 0.27, is from about 0.25 to about 0.26, or from about 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, and preferably 0.39.

According to another embodiment, the time in suspension of the cuttlefish bone powder is from about 5 to about 8 hours, or from about 5 to about 7.5, or from about 5 to about 7, or from about 5 to about 6.5, or from about 5 to about 6, or from about 5 to about 5.5, about 5.5 to about 8 hours, or from about 5.5 to about 7.5, or from about 5.5 to about 7, or from about 5.5 to about 6.5, or from about 5.5 to about 6, about 6.0 to about 8 hours, or from about 6.0 to about 7.5, or from about 6.0 to about 7, or from about 6.0 to about 6.5, about 6.5 to about 8 hours, or from about 6.5 to about 7.5, or from about 6.5 to about 7, about 7.0 to about 8 hours, or from about 7.0 to about 7.5, about 7.5 to about 8 hours, and preferably 5, 5.5, 6, 6.5, 7.0, 7.5, 8, and most preferably 6.5 hours.

The compositions of the present invention are suitable for eliminating tartar, or at least help reduce the presence of dental tartar. Furthermore, the compositions of the present invention do not include any source of fluoride ions. Fluoride containing products have a normally low pH around 4.5, which favors its action, but contributes to demineralization of the enamel and root. The cuttlefish bone power component of the present invention contains a high amount of calcium, which may on the contrary contribute to remineralization of the enamel and root.

The compositions of the present invention may contribute to teeth whitening without further addition of hydrogen peroxide, nor hexametaphosphate, tripolyphosphate, or enzymes which are currently part of whitening toothpaste compositions.

According to embodiments of the present invention, the cuttlefish bone powder described above may represent from about 3% to about 25% (w/w), or from about 3% to about 24%, or from about 3% to about 23%, or from about 3% to about 22%, or from about 3% to about 21%, or from about 3% to about 20%, or from about 3% to about 19%, or from about 3% to about 18%, or from about 3% to about 17%, or from about 3% to about 16%, or from about 3% to about 15%, or from about 3% to about 14%, or from about 3% to about 13%, or from about 3% to about 12%, or from about 3% to about 11%, or from about 3% to about 10%, or from about 3% to about 9%, or from about 3% to about 8%, or from about 3% to about 7%, or from about 3% to about 6%, or from about 3% to about 5%, or from about 3% to about 4%, or from about 4% to about 25% (w/w), or from about 4% to about 24%, or from about 4% to about 23%, or from about 4% to about 22%, or from about 4% to about 21%, or from about 4% to about 20%, or from about 4% to about 19%, or from about 4% to about 18%, or from about 4% to about 17%, or from about 4% to about 16%, or from about 4% to about 15%, or from about 4% to about 14%, or from about 4% to about 13%, or from about 4% to about 12%, or from about 4% to about 11%, or from about 4% to about 10%, or from about 4% to about 9%, or from about 4% to about 8%, or from about 4% to about 7%, or from about 4% to about 6%, or from about 4% to about 5%, or from about 5% to about 25% (w/w), or from about 5% to about 24%, or from about 5% to about 23%, or from about 5% to about 22%, or from about 5% to about 21%, or from about 5% to about 20%, or from about 5% to about 19%, or from about 5% to about 18%, or from about 5% to about 17%, or from about 5% to about 16%, or from about 5% to about 15%, or from about 5% to about 14%, or from about 5% to about 13%, or from about 5% to about 12%, or from about 5% to about 11%, or from about 5% to about 10%, or from about 5% to about 9%, or from about 5% to about 8%, or from about 5% to about 7%, or from about 5% to about 6%, or from about 6% to about 25% (w/w), or from about 6% to about 24%, or from about 6% to about 23%, or from about 6% to about 22%, or from about 6% to about 21%, or from about 6% to about 20%, or from about 6% to about 19%, or from about 6% to about 18%, or from about 6% to about 17%, or from about 6% to about 16%, or from about 6% to about 15%, or from about 6% to about 14%, or from about 6% to about 13%, or from about 6% to about 12%, or from about 6% to about 11%, or from about 6% to about 10%, or from about 6% to about 9%, or from about 6% to about 8%, or from about 6% to about 7%, or from about 7% to about 25% (w/w), or from about 7% to about 24%, or from about 7% to about 23%, or from about 7% to about 22%, or from about 7% to about 21%, or from about 7% to about 20%, or from about 7% to about 19%, or from about 7% to about 18%, or from about 7% to about 17%, or from about 7% to about 16%, or from about 7% to about 15%, or from about 7% to about 14%, or from about 7% to about 13%, or from about 7% to about 12%, or from about 7% to about 11%, or from about 7% to about 10%, or from about 7% to about 9%, or from about 7% to about 8%, or from about 8% to about 25% (w/w), or from about 8% to about 24%, or from about 8% to about 23%, or from about 8% to about 22%, or from about 8% to about 21%, or from about 8% to about 20%, or from about 8% to about 19%, or from about 8% to about 18%, or from about 8% to about 17%, or from about 8% to about 16%, or from about 8% to about 15%, or from about 8% to about 14%, or from about 8% to about 13%, or from about 8% to about 12%, or from about 8% to about 11%, or from about 8% to about 10%, or from about 8% to about 9%, or from about 9% to about 25% (w/w), or from about 9% to about 24%, or from about 9% to about 23%, or from about 9% to about 22%, or from about 9% to about 21%, or from about 9% to about 20%, or from about 9% to about 19%, or from about 9% to about 18%, or from about 9% to about 17%, or from about 9% to about 16%, or from about 9% to about 15%, or from about 9% to about 14%, or from about 9% to about 13%, or from about 9% to about 12%, or from about 9% to about 11%, or from about 9% to about 10%, or from about 10% to about 25% (w/w), or from about 10% to about 24%, or from about 10% to about 23%, or from about 10% to about 22%, or from about 10% to about 21%, or from about 10% to about 20%, or from about 10% to about 19%, or from about 10% to about 18%, or from about 10% to about 17%, or from about 10% to about 16%, or from about 10% to about 15%, or from about 10% to about 14%, or from about 10% to about 13%, or from about 10% to about 12%, or from about 10% to about 11%, or from about 11% to about 25% (w/w), or from about 11% to about 24%, or from about 11% to about 23%, or from about 11% to about 22%, or from about 11% to about 21%, or from about 11% to about 20%, or from about 11% to about 19%, or from about 11% to about 18%, or from about 11% to about 17%, or from about 11% to about 16%, or from about 11% to about 15%, or from about 11% to about 14%, or from about 11% to about 13%, or from about 11% to about 12%, or from about 12% to about 25% (w/w), or from about 12% to about 24%, or from about 12% to about 23%, or from about 12% to about 22%, or from about 12% to about 21%, or from about 12% to about 20%, or from about 12% to about 19%, or from about 12% to about 18%, or from about 12% to about 17%, or from about 12% to about 16%, or from about 12% to about 15%, or from about 12% to about 14%, or from about 12% to about 13%, or from about 13% to about 25% (w/w), or from about 13% to about 24%, or from about 13% to about 23%, or from about 13% to about 22%, or from about 13% to about 21%, or from about 13% to about 20%, or from about 13% to about 19%, or from about 13% to about 18%, or from about 13% to about 17%, or from about 13% to about 16%, or from about 13% to about 15%, or from about 13% to about 14%, or from about 14% to about 25% (w/w), or from about 14% to about 24%, or from about 14% to about 23%, or from about 14% to about 22%, or from about 14% to about 21%, or from about 14% to about 20%, or from about 14% to about 19%, or from about 14% to about 18%, or from about 14% to about 17%, or from about 14% to about 16%, or from about 14% to about 15%, or from about 15% to about 25% (w/w), or from about 15% to about 24%, or from about 15% to about 23%, or from about 15% to about 22%, or from about 15% to about 21%, or from about 15% to about 20%, or from about 15% to about 19%, or from about 15% to about 18%, or from about 15% to about 17%, or from about 15% to about 16%, or from about 16% to about 25% (w/w), or from about 16% to about 24%, or from about 16% to about 23%, or from about 16% to about 22%, or from about 16% to about 21%, or from about 16% to about 20%, or from about 16% to about 19%, or from about 16% to about 18%, or from about 16% to about 17%, or from about 17% to about 25% (w/w), or from about 17% to about 24%, or from about 17% to about 23%, or from about 17% to about 22%, or from about 17% to about 21%, or from about 17% to about 20%, or from about 17% to about 19%, or from about 17% to about 18%, or from about 18% to about 25% (w/w), or from about 18% to about 24%, or from about 18% to about 23%, or from about 18% to about 22%, or from about 18% to about 21%, or from about 18% to about 20%, or from about 18% to about 19%, or from about 19% to about 25% (w/w), or from about 19% to about 24%, or from about 19% to about 23%, or from about 19% to about 22%, or from about 19% to about 21%, or from about 19% to about 20%, or from about 20% to about 25% (w/w), or from about 20% to about 24%, or from about 20% to about 23%, or from about 20% to about 22%, or from about 20% to about 21%, or from about 21% to about 25% (w/w), or from about 21% to about 24%, or from about 21% to about 23%, or from about 21% to about 22%, or from about 22% to about 25% (w/w), or from about 22% to about 24%, or from about 22% to about 23%, or from about 23% to about 25% (w/w), or from about 23% to about 24%, or from about 24% to about 25% (w/w), of the composition. Preferred embodiments may comprise from about 4.3%, 5%, 6.3%, 8.5%, 10%, 11.2%, 12%, 15%, and 15.2% w/w.

The composition of the present invention may comprise a number of ingredients, which include:

Abrasives

According to an embodiment, the personal care composition of the present invention may contain an abrasive in addition to the cuttlefish bone powder used in the present invention. Preferably, the abrasive is chosen from colloidal calcium or colloidal silica. Suitable abrasive include hydrated silica and sodium bicarbonate ($NaHCO_3$). Other suitable abrasives include but are not limited to aluminum hydroxide ($Al(OH)_3$), calcium carbonate ($CaCO_3$), various calcium hydrogen phosphates ($CaHPO_4.2H_2O$, or anhydrous), various silicas (such as fumed silica, precipitated silica) and zeolites, and hydroxyapatite ($Ca_5(PO_4)_3OH$).

Abrasive are insoluble particles that help remove tartar (plaque) from the teeth, and help remove dead cells from the skin. In toothpaste systems, the abrasive silica was shown to be the principal tooth cleaning and abrasive agent.

According to an embodiment abrasives may constitute from about 0.100% to about 0.325%, or from about 0.100% to about 0.300%, or from about 0.100% to about 0.275%, or from about 0.100% to about 0.250%, or from about 0.100% to about 0.225%, or from about 0.100% to about 0.200%, or from about 0.100% to about 0.175%, or from about 0.100% to about 0.150%, or from about 0.100% to about 0.125%, or 0.125% to about 0.325%, or from about 0.125% to about 0.300%, or from about 0.125% to about 0.275%, or from about 0.125% to about 0.250%, or from about 0.125% to about 0.225%, or from about 0.125% to about 0.200%, or from about 0.125% to about 0.175%, or from about 0.125% to about 0.150%, or 0.150% to about 0.325%, or from about 0.150% to about 0.300%, or from about 0.150% to about 0.275%, or from about 0.150% to about 0.250%, or from about 0.150% to about 0.225%, or from about 0.150% to about 0.200%, or from about 0.150% to about 0.175%, or 0.175% to about 0.325%, or from about 0.175% to about 0.300%, or from about 0.175% to about 0.275%, or from about 0.175% to about 0.250%, or from about 0.175% to about 0.225%, or from about 0.175% to about 0.200%, or 0.200% to about 0.325%, or from about 0.200% to about 0.300%, or from about 0.200% to about 0.275%, or from about 0.200% to about 0.250%, or from about 0.200% to about 0.225%, or 0.225% to about 0.325%, or from about 0.225% to about 0.300%, or from about 0.225% to about 0.275%, or from about 0.225% to about 0.250%, or 0.250% to about 0.325%, or from about 0.250% to about 0.300%, or from about 0.250% to about 0.275%, or 0.275% to about 0.325%, or from about 0.275% to about 0.300%, or 0.300% to about 0.325% (w/w) of the composition of the present invention. According to an embodiment, the colloidal calcium may be from about 0.100% to about 0.275% (w/w) of the composition. According to another embodiment, the colloidal silica may be from about 0.02% to about 0.08% (w/w) of the composition.

Thickening Agents

According to an embodiment, the personal care composition of the present invention may contain a thickening agent.

Thickening agents, or thickeners, are substances which increase the viscosity of a solution or liquid/solid mixture without substantially modifying its other properties; although most frequently applied to foods where the target property is taste, the term also is applicable to paints, inks, explosives, etc. Thickeners may also be referred to as "natural gums". Thickeners may also improve the suspension of other ingredients or emulsions which increases the stability of the product. Thickening agents are often regulated as food additives and as cosmetics and personal hygiene product ingredients. Some thickening agents are gelling agents (gellants), forming a gel, dissolving in the liquid phase as a colloid mixture that forms a weakly cohesive internal structure. Examples of suitable thickeners include but are not limited to natural gums obtained from seaweeds, such as agar (E406), alginic acid (E400) and Sodium alginate (E401), potassium alginate, ammonium alginate, calcium alginate, carrageenan (E407); natural gums obtained from non-marine botanical resources, acacia gum, gum arabic (E414), gum ghatti, gum tragacanth (E413), karaya gum (E416), guar gum (E412), locust bean gum (E410), beta-glucan, chicle gum, dammar gum, Glucomannan (E425), mastic gum, *psyllium* seed husks, spruce gum, tara gum (E417); natural gums produced by bacterial fermentation: gellan gum (E418), Xanthan gum (E415).

Also included are starches, pectins, carboxymethyl celluloses, hydroxypropyl celluloses, methyl cellulose and gelatin. Cellulose gum is the common name for carboxymethylcellulose, or CMC. Its emulsifying properties make it especially useful for products with ingredients that tend to separate, such as yogurt and jellies. Its ability to bind water makes it especially useful for diet foods, which tend to substitute water or other liquids for fat. Cellulose gum also improves texture, so it is a common ingredient in ice cream and frosting, products in which smoothness is a mark of quality. Beer manufacturers also use cellulose gum to stabilize beer foam. These same properties are useful for some pharmaceutical products that tend to separate over time, such as toothpaste. In the cosmetics industry, cellulose gum appears in bath products, makeup, shaving gels and hair products. According to an embodiment, the preferred thickening agents include but are not limited to xanthan gum, carboxymethylcellulose, and guar gum.

According to another embodiment, the thickening agent may be present in the formulation in about 2% to about 66% (w/w), or from about 5% to about 66% (w/w), or from about 10% to about 66% (w/w), or from about 15% to about 66% (w/w), or from about 20% to about 66% (w/w), or from about 25% to about 66% (w/w), or from about 30% to about 66% (w/w), or from about 35% to about 66% (w/w), or from about 40% to about 66% (w/w), or from about 45% to about 66% (w/w), or from about 50% to about 66% (w/w), or from about 55% to about 66% (w/w), or from about 60% to about 66% (w/w), or from about 2% to about 60% (w/w), or from about 5% to about 60% (w/w), or from about 10% to about 60% (w/w), or from about 15% to about 60% (w/w), or from about 20% to about 60% (w/w), or from about 25% to about 60% (w/w), or from about 30% to about 60% (w/w), or from about 35% to about 60% (w/w), or from about 40% to about 60% (w/w), or from about 45% to about 60% (w/w), or from about 50% to about 60% (w/w), or from about 55% to about 60% (w/w), or from about 2% to about 55% (w/w), or from about 5% to about 55% (w/w), or from about 10% to about 55% (w/w), or from about 15% to about 55% (w/w), or from about 20% to about 55% (w/w), or from about 25% to about 55% (w/w), or from about 30% to about 55% (w/w), or from about 35% to about 55% (w/w), or from about 40% to about 55% (w/w), or from about 45% to about 55% (w/w), or from about 50% to about 55% (w/w), or from about 2% to about 50% (w/w), or from about 5% to about 50% (w/w), or from about 10% to about 50% (w/w), or from about 15% to about 50% (w/w), or from about 20% to about 50% (w/w), or from about 25% to about 50% (w/w), or from about 30% to about 50% (w/w), or from about 35% to about 50% (w/w), or from about 40% to about 50% (w/w), or from about 45% to about 50% (w/w), or from about 2% to about 45% (w/w), or from about 5% to about 45% (w/w), or from about 10% to about 45% (w/w), or from about 15% to about 45% (w/w), or from about 20% to about 45% (w/w), or from about 25% to about 45% (w/w), or from about 30% to about 45% (w/w), or from about 35% to about 45% (w/w), or from about 40% to about 45% (w/w), or from about 2% to about 40% (w/w), or from about 5% to about 40% (w/w), or from about 10% to about 40% (w/w), or from about 15% to about 40% (w/w), or from about 20% to about 40% (w/w), or from about 25% to about 40% (w/w), or from about 30% to about 40% (w/w), or from about 35% to about 40% (w/w), or from about 2% to about 35% (w/w), or from about 5% to about 35% (w/w), or from about 10% to about 35% (w/w), or from about 15% to about 35% (w/w), or from about 20% to about 35% (w/w), or from about 25% to about 35% (w/w), or from about 30% to about 35% (w/w), or from about 2% to about 30% (w/w), or from about 5% to about 30% (w/w), or from about 10% to about 30% (w/w), or from about 15% to about 30% (w/w), or from about 20% to about 30% (w/w), or from about 25% to about 30% (w/w), or from about 2% to about 25% (w/w), or from about 5% to about 25% (w/w), or from about 10% to about 25% (w/w), or from about 15% to about 25% (w/w), or from about 20% to about 25% (w/w), or from about 2% to about 20% (w/w), or from about 5% to about 20% (w/w), or from about 10% to about 20% (w/w), or from about 15% to about 20% (w/w), or from about 2% to about 15% (w/w), or from about 5% to about 15% (w/w), or from about 10% to about 15% (w/w), or from about 2% to about 10% (w/w), or from about 5% to about 10% (w/w), or from about 2% to about 5% (w/w). According to an embodiment, the concentration is about 2.2% (w/w).

Humectants

According to another embodiment, the composition of the present invention may further comprise a humectant. Humectants are substance used to keep things moist. When used as a food additive, the humectant has the effect of keeping the foodstuff moist. Humectants are also found in many cosmetic products where moisturization is desired, including treatments such as moisturizing hair conditioners and also commonly used in body lotions. Examples of humectants include but are not limited to propylene glycol, as well as hexylene glycol and butylene glycol, glyceryl triacetate, vinyl alcohol, neoagarobiose, sugar polyols such as glycerol, sorbitol, xylitol and maltitol, polymeric polyols like polydextrose, polyethylene glycol, polypropylene glycol, and poly(tetramethylene ether) glycol, *quillaia*, lactic acid, urea, glycerin, aloe vera gel, MP Diol, alpha hydroxy acids like lactic acid, and honey. According to another embodiment, the preferred humectant may glycerin.

According to another embodiment of the present invention, the humectant may be from about 2% to about 5% (w/w), or from about 2% to about 4% (w/w), or from about 2% to about 3% (w/w), or from about 3% to about 5% (w/w), or from about 3% to about 4% (w/w), or from about 4% to about 5% (w/w) of the composition.

Emulsifier

According to an embodiment, the composition of the present invention may further comprise an emulsifier. An emulsifier is a substance that stabilizes an emulsion by increasing its kinetic stability. According to an embodiment, the emulsifier may be a lecithin, a vegetal pulp powder (such as citrus pulp powder, baobab pulp powder, mango pulp powder, tomato pulp powder, pumpkin pulp powder, guava pulp powder, papaya pulp powder and beet pulp powder), sodium citrate (e.g. trisodium citrate) and citric acid. The preferred emulsifier is sodium citrate.

According to another embodiment of the present invention, the emulsifier may be from about 4% to about 10% (w/w) or from about 4% to about 9%, or from about 4% to about 8%, or from about 4% to about 7%, or from about 4% to about 6%, or from about 4% to about 5%, or from about 5% to about 10%, or from about 5% to about 9%, or from about 5% to about 8%, or from about 5% to about 7%, or from about 5% to about 6%, or from about 6% to about 10%, or from about 6% to about 9%, or from about 6% to about 8%, or from about 6% to about 7%, or from about 7% to about 10%, or from about 7% to about 9%, or from about 7% to about 8%, or from about 8% to about 10%, or from about 8% to about 9%, or from about 9% to about 10% of the composition.

Surfactants

According to an embodiment, the composition of the present invention may further comprise a surfactant. Surfactants are often, but always included in toothpaste and other oral care compositions. For example, toothpastes may contain sodium lauryl sulfate (SLS, also known as sodium dodecyl sulfate, SDS) or related surfactants (detergents). SLS is found in many other personal care products, as well, such as shampoo, and is mainly a foaming agent, which enables uniform distribution of toothpaste, improving its cleansing power. Other suitable surfactants include, but are not limited to ammonium lauryl sulfate, sodium N-lauryl sarcosinate (also known as sodium sarcosinate, and sodium lauryl sarcosinate) and sodium lauryl sulfoacetate.

Surfactants (detergents) also help clean the teeth, and provide foam that helps to carry away debris. Moreover, lauryl sulfates have significant anti-bacterial properties, and they can penetrate and dissolve plaque.

According to an embodiment, the surfactant may be from about 1% to about 3% (w/w), or from about 2% to about 3% (w/w), or from about 1% to about 2% (w/w) of surfactant.

pH Regulator

According to an embodiment, the compositions of the present invention may contain a pH regulator. The product pH influences its stability and quality. When the pH is very acid, demineralization is favored, but if it is too basic, calcareous (tartar) deposits on the tooth can become important. Thus, the pH is preferably close to neutral pH, for example from about 6 to about 8, or from about 6.5, to about 7.5, or from about 6.75 to about 7.25, or about 7.0. The measured pH of the product is close to 6.8, or more specifically 6.78.

In embodiment, the pH regulator is an acid or a base which when added to the formulation stabilizes the pH at a desired level suitable for the oral care formulation of the present invention. Suitable pH regulator include but are not limited to citric acid and its derivatives, phosphoric acid and its derivatives, trisodium phosphate, sodium citrate, lactic acid, bicarbonic acid. The pH regulator may be present in concentrations of about 0.1% to about 0.28% (w/w), or from about 0.1% to about 0.25%, or from about 0.1% to about 0.2%, or from about 0.1% to about 0.15%, or from about 0.1% to about 0.12%, or about 0.12% to about 0.28%, or from about 0.12% to about 0.25%, or from about 0.12% to about 0.2%, or from about 0.12% to about 0.15%, or about 0.15% to about 0.28%, or from about 0.15% to about 0.25%, or from about 0.15% to about 0.2%, or about 0.2% to about 0.28%, or from about 0.2% to about 0.25%, or about 0.25% to about 0.28% (w/w) of the composition.

Preservative

According to an embodiment, the compositions of the present invention may contain preservative agent. According to an embodiment, the preservative agent may sometime also act as an active antimicrobial agent for having an active role in the use of the composition.

Microorganisms can feed on humectants and thickening agents and ingredients to restrict their growth may be present in toothpaste. Generally, this is accomplished through minimal water and use of preservatives in the formulation. The most common preservatives in toothpaste are sorbitan sesquioleate derivatives, sodium benzoate, and benzoic acid. However, the compositions of the present invention may also be formulated with natural ingredients with preservative qualities or non-synthetic versions of common preservatives. Examples of natural products having preservative qualities include but is not limited to eucalyptus extract, essential oil having natural antimicrobial properties, such as eucalyptus oil, thyme oil, oregano oil, lemon oil, orange oil, and the likes, as well as natural antimicrobial agents such as thymol, carvacrol, eugenol, eucalyptol, menthol, etc., which are contained in these essential oils, or may be provided as isolated compounds. The composition may contain from about 0.2% to about 2%, and preferably about 0.5% w/w preservative.

Solvents

According to another embodiment of the present invention, the compositions may comprise suitable solvents to formulate the compositions as mouthwashes, for example. Suitable solvents include but are not limited to water, ethanol, isopropanol, sorbitol and glycerin.

According to an embodiment, the composition may contain from about 60% to about 99% (w/w) of the solvent, or from about 70% to about 99% (w/w), or from about 80% to about 99% (w/w), or from about 90% to about 99% (w/w) of the solvent.

Antimicrobial Agents

Antimicrobial agents that are useful in the present invention are the so-called "natural" antimicrobial actives. Such antimicrobial agents include natural essential oils and the individual antimicrobial compounds comprised in these oils. These actives derive their names from their natural occurrence in plants. Essential oils include oils derived from herbs, flowers, trees, and other plants. Such oils are typically present as tiny droplets between the plant's cells, and can be extracted by several methods known to those of skill in the art (e.g., steam distillation, enfleurage (i.e., extraction using fat(s)), maceration, solvent extraction, or mechanical pressing). Essential oils are typically named by the plant or vegetable in which the oil is found. For example, rose oil or peppermint oil is derived from rose or peppermint plants, respectively. Non-limiting examples of essential oils that can be used in the context of the present invention include oils of anise, lemon oil, orange oil, oregano, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea origanum oil, Hydastis carradensis oil, Berberidaceae daceae oil, Ratanhiae and Curcuma longa oil, sesame oil, macadamia nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Other essential oils known to those of skill in the art are also contemplated as being useful within the context of the present invention (e.g., International Cosmetic Ingredient Dictionary, 10th edition, 2004, which is incorporated by reference). Also included in this class of essential oils are the key chemical components of the plant oils that have been found to provide the antimicrobial benefit (e.g., antimicrobial phenolic compounds).

The antimicrobial phenolic compounds of natural origin as used in the present invention can be synthetically made by known methods within the capacity of a skilled technician, or can be obtained from plant oil extracts. In an embodiment of the present invention, the phenolic compounds of natural origin are obtained from plant extracts. In a further embodiment of the present invention, the phenolic compounds of natural origin are commercially available. In yet further embodiments of the present invention, the phenolic compounds of natural origin comprise carvacrol, thymol, eugenol, eucalyptol, menthol, etc.

In an embodiment, the disinfectant formulations of the present invention comprise thymol, carvacrol or mixtures thereof. In a further embodiment, the disinfectant formulations of the present invention comprise one or more natural essential oils enriched in thymol, carvacrol or mixtures of thymol and carvacrol.

The compositions of the present inventions may contain from about 0.01% to about 10% (w/w), or from about 0.01% to about 9% (w/w), or from about 0.01% to about 8% (w/w), or from about 0.01% to about 7% (w/w), or from about 0.01% to about 6% (w/w), or from about 0.01% to about 5% (w/w), or from about 0.01% to about 4% (w/w), or from about 0.01% to about 3% (w/w), or from about 0.01% to about 2% (w/w), or from about 0.01% to about 1% (w/w), or from about 0.01% to about 0.75% (w/w), or from about 0.01% to about 0.5% (w/w), or from about 0.01% to about 0.25% (w/w), or from about 0.01% to about 0.10% (w/w), or from about 0.10% to about 10% (w/w), or from about 0.10% to about 9% (w/w), or from about 0.10% to about 8% (w/w), or from about 0.10% to about 7% (w/w), or from about 0.10% to about 6% (w/w), or from about 0.10% to about 5% (w/w), or from about 0.10% to about 4% (w/w), or from about 0.10% to about 3% (w/w), or from about 0.10% to about 2% (w/w), or from about 0.10% to about 1% (w/w), or from about 0.10% to about 0.75% (w/w), or from about 0.10% to about 0.5% (w/w), or from about 0.10% to about 0.25% (w/w), or from about 0.25% to about 10% (w/w), or from about 0.25% to about 9% (w/w), or from about 0.25% to about 8% (w/w), or from about 0.25% to about 7% (w/w), or from about 0.25% to about 6% (w/w), or from about 0.25% to about 5% (w/w), or from about 0.25% to about 4% (w/w), or from about 0.25% to about 3% (w/w), or from about 0.25% to about 2% (w/w), or from about 0.25% to about 1% (w/w), or from about 0.25% to about 0.75% (w/w), or from about 0.25% to about 0.5% (w/w), or from about 0.50% to about 10% (w/w), or from about 0.50% to about 9% (w/w), or from about 0.50% to about 8% (w/w), or from about 0.50% to about 7% (w/w), or from about 0.50% to about 6% (w/w), or from about 0.50% to about 5% (w/w), or from about 0.50% to about 4% (w/w), or from about 0.50% to about 3% (w/w), or from about 0.50% to about 2% (w/w), or from about 0.50% to about 1% (w/w), or from about 0.50% to about 0.75% (w/w), or from about 0.75% to about 10% (w/w), or from about 0.75% to about 9% (w/w), or from about 0.75% to about 8% (w/w), or from about 0.75% to about 7% (w/w), or from about 0.75% to about 6% (w/w), or from about 0.75% to about 5% (w/w), or from about 0.75% to about 4% (w/w), or from about 0.75% to about 3% (w/w), or from about 0.75% to about 2% (w/w), or from about 0.75% to about 1% (w/w), or from about 1% to about 10% (w/w), or from about 1% to about 9% (w/w), or from about 1% to about 8% (w/w), or from about 1% to about 7% (w/w), or from about 1% to about 6% (w/w), or from about 1% to about 5% (w/w), or from about 1% to about 4% (w/w), or from about 1% to about 3% (w/w), or from about 1% to about 2% (w/w), or from about 2% to about 10% (w/w), or from about 2% to about 9% (w/w), or from about 2% to about 8% (w/w), or from about 2% to about 7% (w/w), or from about 2% to about 6% (w/w), or from about 2% to about 5% (w/w), or from about 2% to about 4% (w/w), or from about 2% to about 3% (w/w), or from about 3% to about 10% (w/w), or from about 3% to about 9% (w/w), or from about 3% to about 8% (w/w), or from about 3% to about 7% (w/w), or from about 3% to about 6% (w/w), or from about 3% to about 5% (w/w), or from about 3% to about 4% (w/w), or from about 4% to about 10% (w/w), or from about 4% to about 9% (w/w), or from about 4% to about 8% (w/w), or from about 4% to about 7% (w/w), or from about 4% to about 6% (w/w), or from about 4% to about 5% (w/w), or from about 5% to about 10% (w/w), or from about 5% to about 9% (w/w), or from about 5% to about 8% (w/w), or from about 5% to about 7% (w/w), or from about 5% to about 6% (w/w), or from about 6% to about 10% (w/w), or from about 6% to about 9% (w/w), or from about 6% to about 8% (w/w), or from about 6% to about 7% (w/w), or from about 7% to about 10% (w/w), or from about 7% to about 9% (w/w), or from about 7% to about 8% (w/w), or from about 8% to about 10% (w/w), or from about 8% to about 9% (w/w), or from about 9% to about 10% (w/w) of antibacterial ingredients.

Flavoring and Sweeteners

The composition of the present invention may contain a flavoring ingredient. The flavoring ingredient may be orange flavoring, apple flavoring, grapefruit flavoring, pineapple flavoring, strawberry flavoring, raspberry flavoring, cranberry flavoring, lime flavoring, lemon flavoring, grape flavoring, peach flavoring, any other fruit flavoring, vanilla flavoring, chocolate flavoring, caramel flavoring, mint flavoring, bubble gum flavoring, or any combination thereof.

Sweeteners such as aspartame, stevia, acesulfame, sucralose, maleic acid, citric acid, and the likes may also be included in the compositions of the present invention.

Other Components

The composition of the present invention may contain other non-active excipients such as pigments and coloring agents, for example titanium oxide or other suitable pigments such as lactoflavins, chlorophylls such as copper derivatives of chlorophylls, and hydrogenated castor oil.

Viscosity of the Composition

According to an embodiment, the viscosity of the oral care composition of the present invention may be from about 17500 to about 35000 cps, preferably 28800 cps, measured at 20° C. in a Brookfield apparatus at 20 rpm. The viscosity of the composition must be so that it does not prevent a good flow and good rinsing. The product is fully soluble in water.

Storage Stability

The stability of the product was measured at 20° C. and 4° C. for 3 months. The product is placed in an oven and the physical and chemical characteristics measured that compare to the initial values. When he shows no phase separation, change in color, odor or deposit, it is considered stable in storage for two years.

Stability to Heat

The heat stability is carried out by the product in an oven at 45° C. for 45 days. it is verified that the physical and chemical parameters are identical to the initial values and the product has no phase change, color or odor. It is considered that the product is stable on storage in the heat.

Density Measurement

Good density ensures gives a good texture to the product and influences it's holding in suspension and stability. The measured value is equal to 1.14 while the desired value is from 1.10 to 1.35.

Preparation of the Cuttlefish Bone Powder

In embodiment, there is provided a method for preparing a cuttlefish bone powder comprising the steps of:
 a) grinding a cuttlefish bone to obtain a coarse cuttlefish bone powder;
 b) sieving the coarse bone powder to obtain a first cuttlefish bone powder having particle size from about 60 microns to about 75 microns;

This is followed by step c, the mild demineralization of the first cuttlefish bone powder having particle size from about 60 microns to about 75 microns at a pH of about 4.5 to about 5.5, at a temperature sufficient and for a time sufficient to obtain a demineralized cuttlefish bone powder. Mild demineralization treatment may be performed, for example in ammonium chloride or ammonium acetate, at pH from about 4.5 to about 5.5, or from about 4.5 to about 5.4, or from about 4.5 to about 5.3, or from about 4.5 to about 5.2, or from about 4.5 to about 5.1, or from about 4.5 to about 5.0, or from about 4.5 to about 4.9, or from about 4.5 to about 4.8, or from about 4.5 to about 4.7, or from about 4.5 to about 4.6, pH from about 4.6 to about 5.5, or from about 4.6 to about 5.4, or from about 4.6 to about 5.3, or from about 4.6 to about 5.2, or from about 4.6 to about 5.1, or from about 4.6 to about 5.0, or from about 4.6 to about 4.9, or from about 4.6 to about 4.8, or from about 4.6 to about 4.7, pH from about 4.7 to about 5.5, or from about 4.7 to about 5.4, or from about 4.7 to about 5.3, or from about 4.7 to about 5.2, or from about 4.7 to about 5.1, or from about 4.7 to about 5.0, or from about 4.7 to about 4.9, or from about 4.7 to about 4.8, pH from about 4.8 to about 5.5, or from about 4.8 to about 5.4, or from about 4.8 to about 5.3, or from about 4.8 to about 5.2, or from about 4.8 to about 5.1, or from about 4.8 to about 5.0, or from about 4.8 to about 4.9, pH from about 4.9 to about 5.5, or from about 4.9 to about 5.4, or from about 4.9 to about 5.3, or from about 4.9 to about 5.2, or from about 4.9 to about 5.1, or from about 4.9 to about 5.0, pH from about 5.0 to about 5.5, or from about 5.0 to about 5.4, or from about 5.0 to about 5.3, or from about 5.0 to about 5.2, or from about 5.0 to about 5.1, pH from about 5.1 to about 5.5, or from about 5.1 to about 5.4, or from about 5.1 to about 5.3, or from about 5.1 to about 5.2, pH from about 5.2 to about 5.5, or from about 5.2 to about 5.4, or from about 5.2 to about 5.3, pH from about 5.3 to about 5.5, or from about 5.3 to about 5.4, pH from about 5.4 to about 5.5, and preferably pH about 4.75, 4.76, 4.77, 4.78, 4.79, 4.80, 4.81, 4.82, 4.83, 4.84, 4.85, 4.86, 4.87, 4.88, 4.89, 4.90, and most preferably 4.86 in order to solubilize unwanted magnesium, ammonia, iron and zinc compounds present in the bone material, and increase the calcium carbonate content of the powder of the present invention. Indeed, the bone powder used in the present invention comprises a high content in calcium; containing at least 95% calcium carbonate, with reduced amounts of magnesium, zinc, iron and ammonia containing derivatives. According to an embodiment, the concentration of ammonium chloride is from about 0.1 M to about 1M. According to another embodiment, the mild demineralization is at a temperature from about 65° C. to about 75° C.

Following the mild demineralization, the demineralized cuttlefish bone powder is washed in step d, until a neutral pH is reached. According to an embodiment, washing the demineralized cuttlefish bone powder is in distilled water.

The demineralized cuttlefish bone powder is then dried (step e). The drying of the demineralized cuttlefish bone powder is for about 30 min to about 60 min., preferably about 55 min. According to an embodiment, drying the demineralized cuttlefish bone powder is at about 200° C. to about 220° C., preferably about 200° C.

The present invention will be more readily understood by referring to the following examples which are given to illustrate the invention rather than to limit its scope.

EXAMPLES

The Examples that follow are illustrative of specific embodiments of the invention, and various uses thereof. They are set forth for explanatory purposes only, and are not to be taken as limiting the invention.

Example 1

Preparation of an Abrasive Agent from Cuttlefish Bones

Cuttlefish bones are cleaned in water, and dried at 50° C. in a stove, and finely ground in a grinder (e.g. a hammer-mill). The resulting powder is sieved at about 60 microns to about 75 microns.

The sieved powder is soaked in a mildly acidic, pH 4.5 solution of 0.1M ammonium chloride, under agitation, to evacuate residual water, which separates from the 0.1M ammonium chloride as a supernatant. The reaction with ammonium chloride causes the demineralization of the bone material, and causes solubilization in the water phase of magnesium, zinc and iron by formation of Magnesium chloride ($MgCl_2$ aq), zinc chloride ($ZnCl_2$ aq) and iron chloride ($FeCl_2$ aq) and ammoniacal species from the bone material, which will remain in solution once the ammonium chloride solution is removed, to yield ultimately a powder material having a calcium carbonate content over 95% (w/w). The reaction may be heated throughout the treatment at about 65° C. to about 75° C. to increase reaction speed and increase purity of the final product. Gaseous by-products include ammonia ($NH_3$) and Hydrogen ($H_2$). The interaction of ion $CO_3^-$ and ion $NH_4^+$ is very strong and gives ion $HCO_3^-$ and $NH_3$ gas. Calcium ions $Ca^{2+}$ will react with the $HCO_3^-$ ions and for the $Ca(HCO_3)_2$ which will finally convert to $CaCO_3$ an provide highly pure powder material.

The obtained powdered material is washed multiple times in water until the water has a neutral pH. The water is completely drained from the powdered material, for example in a screw press or in a centrifuge until all residual water is eliminated. Finally, the powdered material is dried in an oven until completely dried. For example, drying may be performed at 200° C. to about 220° C. for 0.5 to 1 hour. The dried powdered material is loosened, and a preservative agent may be added to the material for long term preservation. Eucalyptus oil, at a concentration of 0.5% (w/w) is a suitable preservative agent.

Example 2

Toothpaste Compositions

A toothpaste composition containing mostly natural products. The composition contains the following ingredients:

| | Ingredient | #1 Amount % (w/w) | #2 Amount % (w/w) | #3 Amount % (w/w) |
|---|---|---|---|---|
| 1. | Cuttlefish bone powder | 11.2 | 8.5 | 15.2 |
| 2. | Xanthane Gum | 2.0 | 0 | 1.2 |
| 3. | Carboxymethylcellulose | 0 | 0.2 | 0.8 |
| 4. | Aluminium silicate | 0.22 | 1.30 | 0 |
| 5. | Sorbitol 70% | 40.45 | 25.5 | 50.25 |
| 6. | Glycerine | 12.5 | 14.1 | 5.10 |
| 7. | Sodium bicarbonate | 0.1 | 1.20 | 0.8 |
| 8. | *Eucalyptus* extract | 0.5 | 0 | |
| 9. | Citronelle essential oil | 0 | 0.8 | 0 |
| 10. | Tea tree extract | 0 | 0 | 0.5 |
| 11. | Hydrated silica | 20.0 | 0 | 0 |
| 12. | titanium oxide | 0 | 0.5 | 0.5 |
| 13. | Sodium citrate | 2.02 | 3.25 | 1.25 |
| 14. | Sodium lauroyl sarcosinate | 1.3 | 1.5 | 1.5 |
| 15. | Mint flavoring | 1.0 | 1.0 | 1.0 |

The composition of this example has a neutral pH from about 6.8 to 7.8, which does not affect the tooth enamel, and does not cause demineralization of the root or enamel. The abrasiveness of the composition is from about 0% to about 85%, which is relatively mild and does not cause abrasion of the dentin, according to the abrasiveness scale of DESAUTELS and LABRECHE which varies as follows for toothpaste: 1) bit abrasive: 0% to 88%; 2) abrasive to medium abrasive: 88% to 100%, and 3) very abrasive: >100%.

The composition will be tested for its properties for tartar removal, teeth whitening, prevention of halitosis, and prevention of dental cavity.

Example 3

Mouthwash Composition

| Ingredient | Amount % (w/w) |
|---|---|
| Cuttlefish bone powder | 4.3 |
| Sorbitol 99% | 8.22 |
| glycerin | 1.09 |
| Sodium saccharin | 0.18 |
| flavouring | 0.8 |
| Hydrogenated castor oil | 2.11 |
| Menthol | 0.01 |
| Citric acid | 0.23 |
| Sodium benzoate | 0.2 |

Example 4

Chewing Gum Composition

| Ingredient | Amount % (w/w) |
|---|---|
| Cuttlefish bone powder | 6.3 |
| Maltitol powder micronised | 87.0 |
| Maltitol powder coloured | 3.12 |
| flavor | 1.6 |
| Maleic acid | 0.4 |
| Citric acid | 0.4 |
| Magnesium stearate | 1.5 |

Example 5

Test of Product Effectiveness

Figure 2:
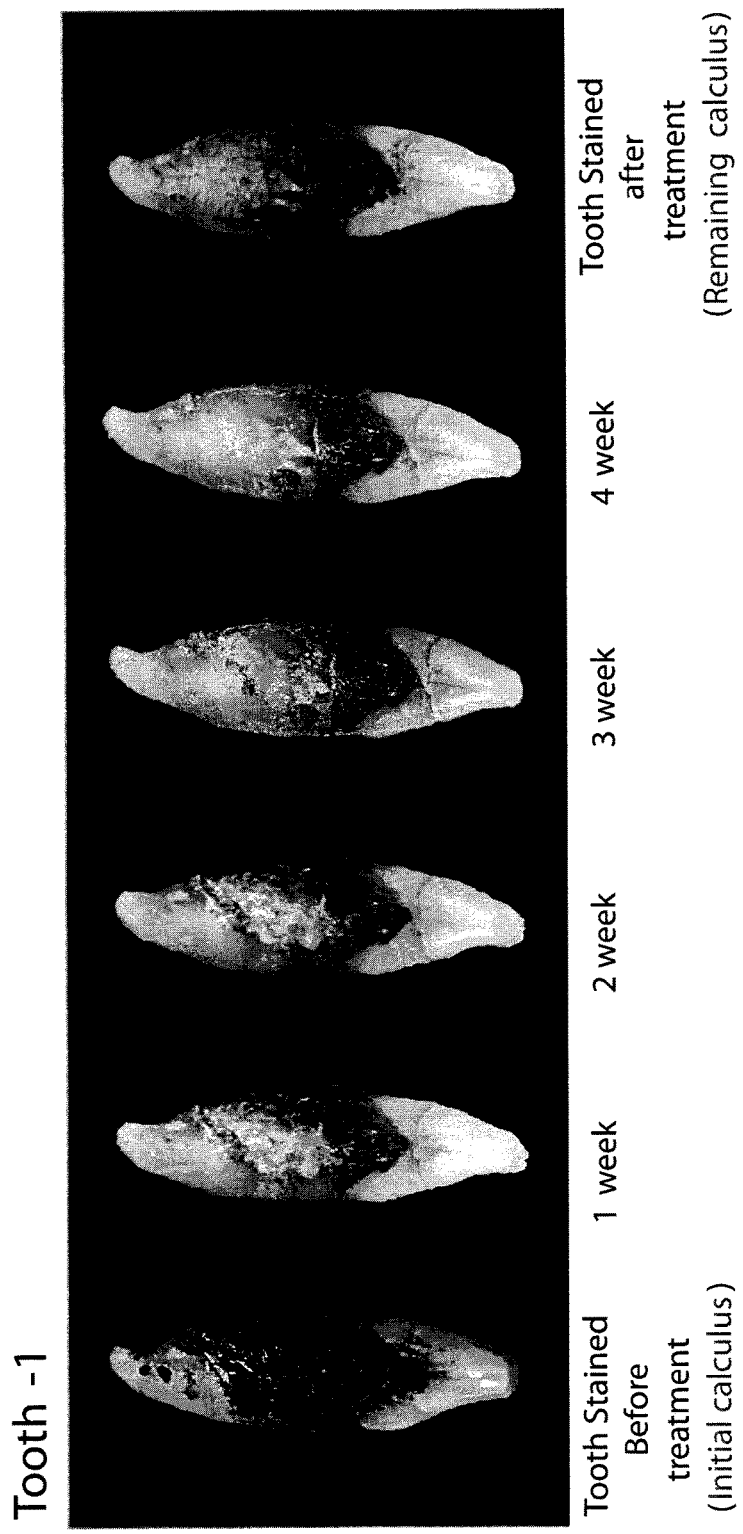
FIG. 2 illustrates the presence of calculus on a tooth before and after having been brushed in a tooth brushing machine with a oral care composition of the present invention.
Figure 3:
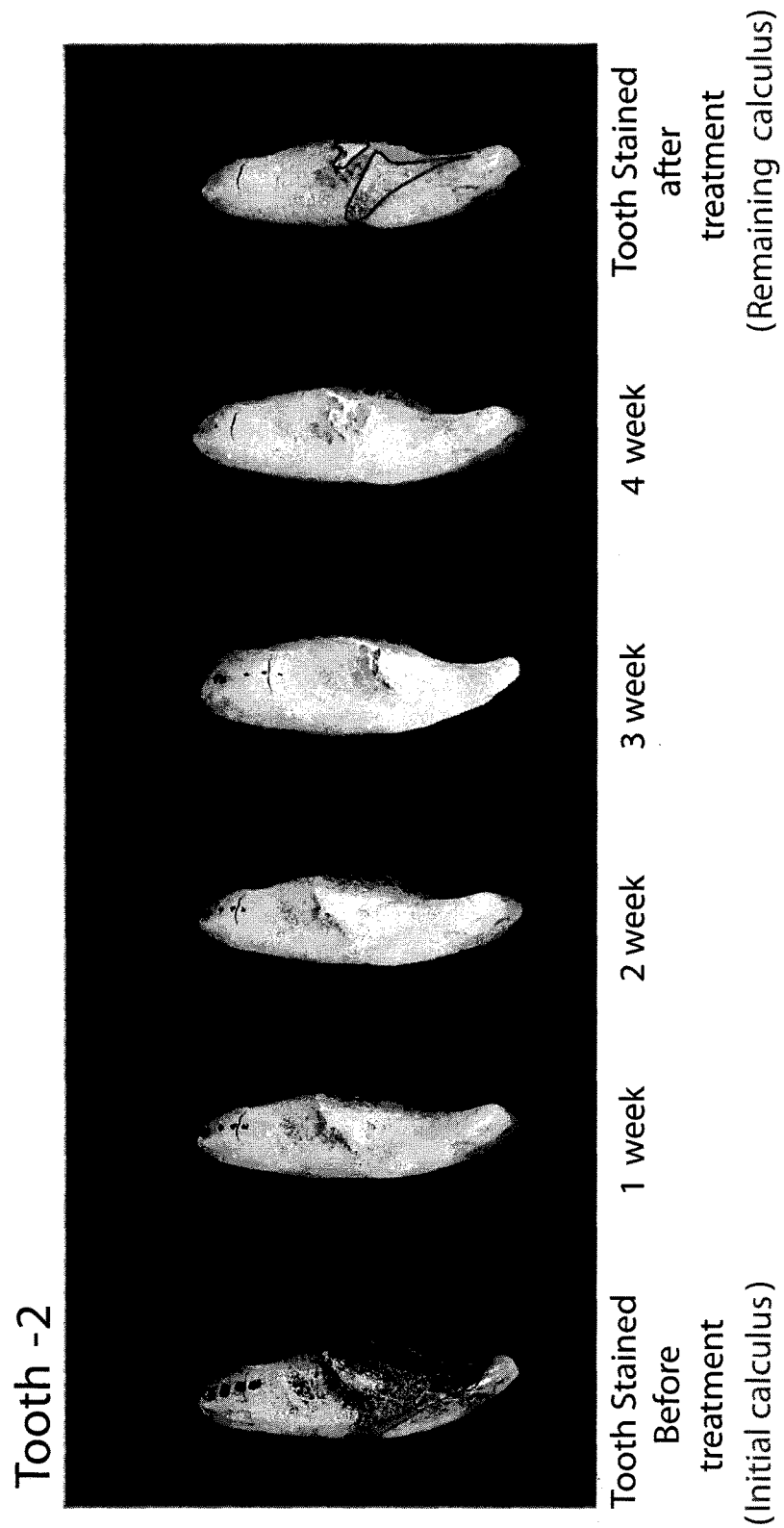
FIG. 3 illustrates the presence of calculus on a tooth before and after having been brushed in a tooth brushing machine with a oral care composition of the present invention.

A composition of the present invention is tested for effectiveness at removing calculus. Lower anterior teeth with dental calculus are collected from adult patients with dental conditions that require tooth extraction. are stained to verify the present of calculus. They are then mounted in an automated tooth brushing apparatus (see FIG. 1). The treatment is carried out by adding 10 ml of the composition of the present invention (composition No. 1 from example 2 above) to the brushing machine and the teeth are brushed for 28, 56, 84 and 112 minutes, at 90 strokes/min (amplitude of 10 mm) under 375 g of applied load. This is equivalent to regular teeth brushing of 2 minutes session, twice a day for 1, 2, 3 and 4 weeks. Referring to FIGS. 2 and 3, the percentage of calculus removed over the period of three weeks is measured at the surface are of remaining calculus after the treatment, each week. The final pictures of the teeth in FIGS. 2 and 3 were taken after what is equivalent to four weeks of cleaning. The composition of the present invention was capable of removing almost 80% of the calculus over the course of the treatment.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. An oral care composition, comprising:
   (a) a cuttlefish bone powder having particles with at least 95% (w/w) calcium carbonate content and a particle size from 60 microns to 61 microns; and
   (b) a suitable carrier.

2. The oral care composition of claim 1, wherein the calcium carbonate content is from 95% (w/w) to about 99.9% (w/w).

3. The oral care composition of claim 1, wherein the cuttlefish bone powder has a relative density of about 0.15 to about 1.30.

4. The oral care composition of claim 1, wherein the cuttlefish bone powder has a porosity of about 0.25 to about 0.45.

5. The oral care composition of claim 1, wherein the cuttlefish bone powder has a suspension time in water of about 5 h to about 8 h.

6. The oral care composition of claim 1, wherein the composition contains from about 0.1% (w/w) to about 20% (w/w) of the cuttlefish bone powder.

7. The oral care composition of claim 1, further comprising:
   (a) an abrasive;
   (b) a thickening agent;
   (c) a humectant;
   (d) an emulsifier;
   (e) a surfactant;
   (f) a pH regulator;
   (g) a solvent;
   (h) an antimicrobial agent; and/or
   (i) a preservative.

8. The oral care composition of claim 7, wherein the abrasive is a colloidal calcium, a colloidal silica, a hydrated silica, a sodium bicarbonate ($NaHCO_3$), aluminum hydroxide ($Al(OH)_3$), calcium carbonate ($CaCO_3$), calcium hydrogen phosphate dihydrate ($CaHPO_4.2H_2O$), an anhydrous calcium hydrogen phosphate, a silica, a zeolite, hydroxyapatite ($Ca_5(PO_4)_3OH$), or a combination thereof.

9. The oral care composition of claim 7, wherein the composition contains from about 0.100% (w/w) to about 0.325% (w/w) of the abrasive.

10. The oral care composition of claim 7, wherein the thickening agent is a natural gum obtained from seaweeds, a natural gum obtained from non-marine botanical resource, a natural gum produced by bacterial fermentation, a starch, a pectin, a carboxymethyl cellulose, a hydroxypropyl cellulose, a methyl cellulose, a gelatin, or a combination thereof.

11. The oral care composition of claim 10, wherein the natural gums obtained from seaweeds is agar, alginic acid, Sodium alginate, potassium alginate, ammonium alginate, calcium alginate, carrageenan, or a combination thereof,
   wherein the natural gum obtained from non-marine botanical resource is acacia gum, gum arabic, gum ghatti, gum tragacanth, karaya gum, guar gum, locust bean gum, beta-glucan, chicle gum, dammar gum, Glucomannan, mastic gum, *psyllium* seed husks, spruce gum, tara gum, or a combination thereof, and
   wherein the natural gum produced by bacterial fermentation is gellan gum, Xanthan gum, or a combination thereof.

12. The oral care composition of claim 7, wherein the composition contains from about 2% (w/w) to about 66% (w/w) of the thickening agent.

13. The oral care composition of claim 7, wherein the humectant is propylene glycol, hexylene glycol, butylene glycol, glyceryl triacetate, neoagarobiose, a sugar polyol, a polymeric polyol, *quillaia*, urea, aloe vera gel, 2-methyl-1,3-propanediol, an alpha hydroxy acid, honey, or glycerin.

14. The oral care composition of claim 7, wherein the composition contains from about 2% (w/w) to about 5% (w/w) of the humectant.

15. The oral care composition of claim 7, wherein the composition contains from about 4% (w/w) to about 10% (w/w) of the emulsifier.

16. The oral composition of claim 7, wherein the surfactant is sodium lauryl sulfate, ammonium lauryl sulfate, sodium N-lauryl sarcosinate, sodium lauryl sulfoacetate, or a combination thereof.

17. The oral composition of claim 7, wherein the composition contains from about 1% (w/w) to about 3% (w/w) of the surfactant.

18. The oral composition of claim 7, wherein the solvent is water, ethanol, isopropanol, sorbitol, or glycerol.

19. The oral composition of claim 18, wherein the composition contains at least about 60% (w/w) of the solvent.

20. A method of cleaning an oral cavity, comprising applying the oral composition of claim 7 to the oral cavity.

21. The oral care composition of claim 8, wherein the colloidal silica is from about 0.02% to about 0.08% (w/w) or from about 0.100% to about 0.275% (w/w) of the composition.

* * * * *